(12) United States Patent
Terasaka et al.

(10) Patent No.: US 8,581,003 B2
(45) Date of Patent: Nov. 12, 2013

(54) PROCESS FOR PRODUCING ALIPHATIC CARBOXYLIC ACID AMIDE

(75) Inventors: Michio Terasaka, Wakayama (JP); Tetsuaki Fukushima, Wakayama (JP)

(73) Assignee: KAO Corporation, Tokyo (JP)

( * ) Notice: Subject to any disclaimer, the term of this patent is extended or adjusted under 35 U.S.C. 154(b) by 227 days.

(21) Appl. No.: 12/741,928

(22) PCT Filed: Oct. 31, 2008

(86) PCT No.: PCT/JP2008/070363
§ 371 (c)(1),
(2), (4) Date: Aug. 6, 2010

(87) PCT Pub. No.: WO2009/063813
PCT Pub. Date: May 22, 2009

(65) Prior Publication Data
US 2010/0298604 A1   Nov. 25, 2010

(30) Foreign Application Priority Data
Nov. 12, 2007  (JP) ................................. 2007-293466

(51) Int. Cl.
*C07C 231/02* (2006.01)
(52) U.S. Cl.
USPC ............................ 564/138; 564/136; 502/350
(58) Field of Classification Search
USPC .................................. 564/135, 138; 502/350
See application file for complete search history.

(56) References Cited

U.S. PATENT DOCUMENTS 3,801,610 A    4/1974   Werdehausen et al.

FOREIGN PATENT DOCUMENTS

| EP | 0 133 590 A1 | 2/1985 |
| EP | 0 239 954 A2 | 10/1987 |
| EP | 0 412 614 A2 | 2/1991 |
| GB | 2 100 732 A | 1/1983 |
| JP | 60-36450 A | 2/1985 |

OTHER PUBLICATIONS

Chinese Office Action dated Sep. 21, 2011 for Application No. 200880113552.6.
Jozef Lukac et al., "Characterization of Zr-doped TiO2 prepared by homogenous co-precipitation without high-temperature treatment", Journal of Materials Science, Kluwer Academic Publishers, BO, vol. 42, No. 22, Jul. 27, 2007, pp. 9421-9428.
Japanese Office Action dated Dec. 18, 2012, and English Translation thereof for Japanese Patent Application No. 2007-293466, 2007.

*Primary Examiner* — Shailendra Kumar
(74) *Attorney, Agent, or Firm* — Birch, Stewart, Kolasch & Birch, LLP

(57) ABSTRACT

The present invention relates to a process for producing an aliphatic carboxylic acid amide, including the step of reacting an aliphatic carboxylic acid or an alkyl ester thereof containing an alkyl group having 1 to 4 carbon atoms with a mono- or dialkylamine containing an alkyl group or groups having 1 to 4 carbon atoms in the presence of a solid acid catalyst containing titanium oxide as a main component and an oxide or oxides of at least one element selected from elements (except titanium) belonging to Groups 4, 5 and 14 of the long form of the periodic table, wherein the catalyst has an average particle diameter of 2 μm or more. The process for producing an aliphatic carboxylic acid amide according to the present invention has a high reaction efficiency of the reaction of the aliphatic carboxylic acid or alkyl ester thereof with the mono- or dialkylamine, and shows an excellent filtration efficiency in separation of the catalyst.

6 Claims, No Drawings

PROCESS FOR PRODUCING ALIPHATIC CARBOXYLIC ACID AMIDE

This application is a 371 of PCT/JP2008/070363, filed Oct. 31, 2008.

FIELD OF THE INVENTION

The present invention relates to a process for producing an aliphatic carboxylic acid amide and, more particularly, to a process for producing an aliphatic carboxylic acid amide by reacting an aliphatic carboxylic acid or its derivative with an alkylamine.

BACKGROUND OF THE INVENTION

A variety of catalysts are generally used for the production of aliphatic carboxylic acid amides from aliphatic carboxylic acids or their alkyl esters.

For example, JPA-47-168 discloses amidation under ambient pressure using as a catalyst a compound of a Group IVb or Group Vb metal, preferably a complex of titanium, zirconium or tantalum. JPA-60-36450 discloses the use of a hydrated oxide of a Group IVa, Group IVb or Group Va element, preferably a hydrated oxide of titanium, zirconium or tin. Further, JPA-2001-270855 discloses a process in which an organic carboxylic acid is reacted with ammonia or a mono- or dialkylamine in the presence of granular titanium dioxide.

SUMMARY OF THE INVENTION

The present invention relates to:
(1) a process for producing an aliphatic carboxylic acid amide, including the step of reacting an aliphatic carboxylic acid or an alkyl ester thereof containing an alkyl group having 1 to 4 carbon atoms with a mono- or dialkylamine containing an alkyl group or groups having 1 to 4 carbon atoms in the presence of a solid acid catalyst containing titanium oxide as a main component and an oxide or oxides of at least one element selected from the group consisting of elements (except titanium) belonging to Groups 4, 5 and 14 of the long form of the periodic table, the catalyst having an average particle diameter of 2 μm or more; and
(2) a solid acid catalyst for use in reacting an aliphatic carboxylic acid or an alkyl ester thereof containing an alkyl group having 1 to 4 carbon atoms with a mono- or dialkylamine containing an alkyl group or groups having 1 to 4 carbon atoms, containing titanium oxide as a main component and an oxide or oxides of at least one element selected from the group consisting of elements (except titanium) belonging to Groups 4, 5 and 14 of the long form of the periodic table, the catalyst having an average particle diameter of 2 μm or more.

DETAILED DESCRIPTION OF THE INVENTION

The activity of the catalysts used in the processes described in the above-described patent documents is still insufficient to provide satisfactory reaction efficiency. Further, when the catalysts described in the above-described patent documents are filtered, after the reaction, for the purpose of separating the used catalysts, etc., the filtration requires high pressure conditions and prolonged process time and cannot be carried out efficiently because of poor filterability of the catalysts.

The present invention is aimed at providing a process for producing an aliphatic carboxylic acid amide, which has high reaction efficiency of the reaction of an aliphatic carboxylic acid or an alkyl ester thereof with a mono- or dialkylamine and which shows excellent filtration efficiency in catalyst separation.

The process for producing an aliphatic carboxylic acid amide according to the present invention includes the step of reacting an aliphatic carboxylic acid or an alkyl ester thereof containing an alkyl group having 1 to 4 carbon atoms with a mono- or dialkylamine containing an alkyl group or groups having 1 to 4 carbon atoms in the presence of a solid acid catalyst which contains titanium oxide as a main component and an oxide or oxides of at least one element selected from the group consisting of elements (except titanium) belonging to Groups 4, 5 and 14 of the long form of the periodic table and which has an average particle diameter of 2 μm or more.

[Solid Acid Catalyst]

The solid acid catalyst used in the present invention contains titanium oxide as a main component and an oxide or oxides of at least one element selected from the group consisting of elements (except titanium) belonging to Group 4, Group 5 and Group 14 of the long form of the periodic table.

The solid acid catalyst used in the present invention contains titanium oxide as a main component. From the viewpoint of good catalytic activity, the content of the titanium oxide in the catalyst is preferably 30% by mass or more, more preferably 42% by mass or more and still more preferably 48% by mass or more in terms of metallic titanium. The upper limit of the titanium oxide content in the catalyst is not particularly limited, and is preferably 60% by mass, more preferably 59.5% by mass and still more preferably 59% by mass in terms of metallic titanium.

In addition to the titanium oxide, the solid acid catalyst used in the present invention contains an oxide or oxides of at least one element selected from the group consisting of elements (except titanium) belonging to Group 4, Group 5 and Group 14 of the long form of the periodic table. The oxides may be used singly or in combination of any two or more thereof. The element belonging to Groups 4, 5 and 14 of the Periodic Table is preferably at least one element selected from the group consisting op zirconium, niobium, silicon and germanium from the viewpoints of good catalytic activity and filterability of the catalyst.

In the solid acid catalyst, the proportion of the oxide or oxides of at least one element selected from the group consisting of elements (except titanium) belonging to Groups 4, 5 and 14 of the Periodic Table relative to the titanium oxide is preferably adjusted such that a mass ratio of the at least one element selected from the group consisting of elements (except titanium) belonging to Groups 4, 5 and 14 of the Periodic Table to titanium is from 0.005 to 0.8 from the viewpoints of good catalytic activity and filterability of the catalyst. The mass ratio is more preferably from 0.01 to 0.7 and still more preferably from 0.02 to 0.6.

In the present invention, the average particle diameter of the solid acid catalyst is 2 μm or more from the viewpoints of good catalytic activity and filterability of the catalyst. As used herein, the term "average particle diameter" is intended to mean a median diameter based on volume. The average particle diameter is preferably 3 μm or more and more preferably 5 μm or more from the viewpoints of good filterability and easiness in handling (prevention of powder scattering) of the catalyst. The upper limit of the average particle diameter of the solid acid catalyst is not particularly limited, and is usually about 20 μm from the viewpoint of good dispersibility of the catalyst in the reaction solution.

The solid acid catalyst also contains particles having a diameter of 1 μm or less in an amount of 30% by volume or less, more preferably 20% by volume or less and still more preferably 15% by volume or less, on the basis of the whole particles from the viewpoint of good filterability thereof.

In the present invention, the particle diameter and particle size distribution of the solid acid catalyst may be measured using a laser diffraction type particle size distribution measuring apparatus. The measuring method is more specifically described hereinafter.

In the present invention, the specific surface area of the solid acid catalyst is not particularly limited, and is preferably 50 m$^2$/g or more, more preferably 100 m$^2$/g or more and still more preferably 150 m$^2$/g or more from the viewpoint of good catalytic activity. The specific surface area may be measured by the ordinary BET method.

In the present invention, there is no specific limitation with respect to the form, etc. of the oxides, and any solid acid catalyst may be used as long as it contains titanium oxide as a main component and an oxide or oxides of at least one element selected from the group consisting of elements (except titanium) belonging to Groups 4, 5 and 14 of the long form of the periodic table. Thus, the catalyst may be in the form of a composite oxide composed of titanium oxide and the oxide or oxides of elements (except titanium) belonging to Groups 4, 5 and 14 of the Periodic Table. Alternatively, titanium may be supported as titanium oxide on a carrier containing the oxide or oxides of elements (except titanium) belonging to Groups 4, 5 and 14 of the Periodic Table. In this case, a method for supporting titanium on the carrier is not particularly limited, and any of conventionally known methods such as, for example, impregnation, precipitation, ion exchange, coprecipitation, and kneading may be suitably selected.

A method for preparing the solid acid catalyst is not particularly limited and may be performed, for example, in a manner as described in (a) and (b) below.

(a) An aqueous solution containing nitrates, sulfates, carbonates, halides, alkoxides or amine complexes, preferably nitrates, sulfates, chlorides or alkoxides, of titanium and element or elements (except titanium) belonging to Groups 4, 5 and 14 of the Periodic Table is prepared. These metal components are simultaneously hydrolyzed to obtain precipitates. The precipitates are subjected to solid-liquid separation by filtration, centrifugation, etc. The obtained solid phase is washed with ion-exchange water and dried. Thereafter, if necessary, the solid is subjected to a calcination treatment at a temperature of preferably from 100 to 600° C., more preferably from 100 to 400° C., for removal of residual counter ions of the starting metal salts or for stabilization of catalytic activity.

(b) In a liquid in which an oxide or oxides of an element or elements (except titanium) belonging to Groups 4, 5 and 14 of the Periodic Table is/are suspended, the above-exemplified salt of titanium is hydrolyzed to obtain precipitates. The precipitates are subjected to solid-liquid separation by filtration, centrifugation, etc. The obtained solid phase is washed with ion-exchange water and dried. Thereafter, if necessary, the solid is subjected to a calcination treatment at a temperature of preferably from 100 to 600° C. and more preferably from 100 to 400° C., for removal of residual counter ions of the starting metal salts or for stabilization of catalytic activity.

[Production of Aliphatic Carboxylic Acid Amide]

As the aliphatic carboxylic acid used in the present invention, there may be mentioned an aliphatic carboxylic acid containing a linear or branched hydrocarbon chain having preferably 6 to 24 carbon atoms, more preferably 6 to 22 carbon atoms and still more preferably 8 to 22 carbon atoms from the viewpoint of usefulness of the obtained aliphatic carboxylic acid amide. Further still more preferred is an aliphatic carboxylic acid containing a linear or branched alkyl chain or alkenyl chain having the above-described carbon number. These aliphatic carboxylic acids may be either saturated or unsaturated and may be used singly or in combination of any two or more thereof. In the alkyl ester (in which the carbon number of the alkyl group is 1 to 4) of the aliphatic carboxylic acid, specific examples of the alkyl group having 1 to 4 carbon atoms include a methyl group, an ethyl group, a propyl group and an isopropyl group. Particularly preferred is a methyl group.

Specific examples of the aliphatic carboxylic acid include aliphatic monocarboxylic acids such as caproic acid, caprylic acid, capric acid, lauric acid, myristic acid, palmitic acid, stearic acid, arachic acid, behenic acid, dimethyloctanoic acid, butylheptylnonanoic acid, hexenoic acid, octenoic acid, decenoic acid, dodecenoic acid, tetradecenoic acid, hexadecenoic acid, octadecenoic acid, eicosenoic acid, docosenoic acid, linoleic acid and linolenic acid, and aliphatic dicarboxylic acids such as adipic acid, azelaic acid, sebacic acid, decamethylenedicarboxylic acid, hexadecamethylenedicarboxylic acid and octadecamethylenedicarboxylic acid. In the present invention, an aliphatic monocarboxylic acid is preferred from the viewpoint of reaction selectivity.

The mono- or dialkylamine containing an alkyl group or groups having 1 to 4 carbon atoms for use in the present invention is a compound containing one or two alkyl groups having 1 to 4 carbon atoms. Specific examples of the monoalkylamine include monomethylamine, monoethylamine, monopropylamine and monobutylamine. Specific examples of the dialkylamine include dimethylamine, diethylamine, methylethylamine and dipropylamine. Among these amines, monomethylamine, monoethylamine, dimethylamine and diethylamine are preferred from the viewpoint of usefulness of the aliphatic carboxylic acid amide, and monomethylamine and dimethylamine are more preferred.

The process for producing an aliphatic carboxylic acid amide according to the present invention may be carried out by a batch, semibatch or continuous method using a suspension bed or by a fixed-bed flow method. In the production process using a batch or semibatch method, an aliphatic carboxylic acid or an alkyl ester thereof is dissolved and charged together with a predetermined amount of a catalyst in a reaction vessel. After the atmosphere of the reaction vessel has been sufficiently replaced with nitrogen, the contents are heated to a temperature at which the reaction is performed. Thereafter, a mono- or dialkylamine gas is flowed into the reaction vessel to produce an amide. In the production process using a continuous method or a fixed-bed flow method, a catalyst is packed and heated to a temperature at which the reaction is performed. Thereafter, a dissolved aliphatic carboxylic acid or an alkyl ester thereof and a mono- or dialkylamine gas are flowed into a reactor to produce an amide.

The reaction of the aliphatic carboxylic acid or alkyl ester thereof with the mono- or dialkylamine may be carried out under a pressurized condition or ambient pressure. The reaction temperature is generally 110 to 300° C. From the viewpoints of reaction efficiency and selectivity, the reaction temperature is preferably 150 to 280° C., more preferably 170 to 270° C.

The mono- or dialkylamine containing an alkyl group or groups having 1 to 4 carbon atoms for use in the present invention is used in an amount of usually from 0.01 to 15 mol/h, preferably from 0.1 to 5 mol/h and more preferably from 0.3 to 3 mol/h per 1 mol of the aliphatic carboxylic acid or alkyl ester thereof.

The catalyst may be used in an arbitrary amount. However, from the viewpoints of good reaction efficiency and selectivity as well as low production costs, the catalyst is usually used in an amount of from 0.01 to 20% by mass, preferably from 0.1 to 15% by mass and more preferably from 0.1 to 10% by mass on the basis of the aliphatic carboxylic acid or alkyl ester thereof.

Since the catalyst of the present invention may exhibit excellent filterability, it is preferred that the catalyst and other impurities be separated and removed from the aliphatic carboxylic acid amide-containing reaction solution obtained in the above reaction step by filtration using a filtering device. Although the filtration temperature and pressure are not particularly limited, from the viewpoint of reducing a viscosity of the reaction product to improve a filtration efficiency thereof, the filtration is preferably conducted at least at a temperature not lower than the melting point of the reaction product, specifically, at a temperature not lower than room temperature. The filtration may be carried out either under an increased pressure or a reduced pressure, and is preferably carried out under an increased pressure of 0.01 MPaG (G: gauge pressure) or more.

In the present invention, the reaction efficiency can be improved and, additionally, the filtration can be efficiently performed under a low pressure within a short period of time by using the catalyst having a high activity as described above.

According to the production process of the present invention, the reaction of an aliphatic carboxylic acid or its alkyl ester thereof with a mono- or dialkylamine can be carried out with a high reaction efficiency. At the same time, the filtration efficiency in the separation of the catalyst can be significantly improved. Therefore, the production process can be performed with a high productivity in an economically advantageous manner.

Since the production process of the present invention exhibits a high reaction efficiency and is excellent in filtration efficiency in separation of the catalyst, the obtained aliphatic carboxylic acid amide may be suitably used, for example, as a raw material of an aliphatic tertiary amine which is an important intermediate in the domestic and industrial application field.

The present invention is described in more detail with reference to the following examples, but it should be noted that these examples are only illustrative and not intended to limit the substance of the present invention thereto.

[Measurement of Physical Properties of Catalyst]

In the following examples, the composition, specific surface area, particle diameter, particle size distribution of the obtained catalyst, etc., were measured by the following methods.

Composition of Catalyst:

Among the constituting elements, the contents of titanium, zirconium and silicon were quantitatively analyzed by fluorescent X-ray measurement, while the contents of the other metal elements were quantitatively analyzed by IPC emission analysis. More specifically, with regard to titanium, zirconium and silicon, 0.1 g of a sample was mixed with 5 g of lithium tetraborate and a releasing agent (lithium carbonate: lithium bromide:lithium nitrate=5:1:5). The mixture was melted at 1,050° C. by alkali fusion to obtain glass beads. The glass beads were analyzed using a wavelength dispersive type fluorescent X-ray spectrometer "ZSX100e" available from Rigaku Corporation. The content of each metal was determined from the obtained X-ray intensity by comparison with a calibration curve obtained from a material prepared by blending high purity samples of the elements in intended concentrations. In the case of the metal elements other than titanium, zirconium and silicon, 0.1 g of a sample was mixed with 2 mL of sulfuric acid, and the resulting mixture was heated. Then, the mixture was further mixed with adequate amounts of hydrogen peroxide and nitric acid, and then heated. These procedures were repeated until a clear solution was obtained. The obtained solution was cooled and placed in a measuring flask, and then messed-up to 50 mL with pure water. The obtained solution was measured for the content of each element using an IPC emission analyzer.

Specific Surface Area of Catalyst:

A sample was heated and thoroughly deaerated at 100° C. and is allowed to absorb nitrogen gas for the measurement of the specific surface area by one-point method using a BET specific surface area measuring device "Flowsorb Model 2300" available from Shimadzu Corporation.

Particle Diameter and Particle Size Distribution of Catalyst:

The particle diameter (based on volume), average particle diameter (medium diameter) and particle size distribution were determined using Laser Diffraction Particle Size Distribution Analyzer "Model LA-500" available from Horiba Ltd.

[Measurement of Acid Value]

In the following examples, an acid value was measured, after being bubbled with nitrogen to purge an amine gas dissolved therein, for the purpose of determining the amount of unreacted aliphatic carboxylic acid remaining in each product obtained by the reaction.

The acid value represents the number of milligrams of potassium hydroxide required for neutralizing a free aliphatic carboxylic acid contained in 1 g of the sample. The measurement thereof is performed according to the testing method described in the official compendium (JIS K0070, AOCS Te 2a-64). That is, a sample was precisely weighed (for example, in an amount of 20 g when the expected acid value was less than 1, and 20 to 5 g when the expected acid value was 1 to 5) and placed in an Erlenmeyer flask. The sample was mixed with and dissolved in about 30 mL of a mixed solvent of toluene (reagent grade) and ethanol (reagent grade) (2:1) which was neutralized to a faint pink color immediately before use by adding a 1% phenolphthalein indicator solution thereto. Meanwhile, the sample may be dissolved using a warm water bath when it is not easily dissolved, and then cooled. The obtained solution was then titrated with a 0.1 mol/L alcoholic potassium hydroxide standard solution. The point up to which the faint pink color was continuously exhibited for 30 s was determined as the endpoint. The acid value was calculated according to the following formula from the amount A (mL) of the alcoholic potassium hydroxide standard solution required for completing the titration, factor f of the alcoholic potassium hydroxide standard solution, coefficient K (=5.611 when 0.1 mol/L alcoholic potassium hydroxide standard solution was used) and amount (g) of the sample weighed:

Acid value=$(A \times f \times K)$/(amount of sample weighed).

PREPARATION EXAMPLE 1

Preparation of Catalyst A

A separable flask was charged with 250 g of isopropanol, to which 44 g of titanium tetraisopropoxide and 2.3 g of an isopropanol solution of zirconium tetrapropoxide (effective content: 75%) were added. The mixture was heated to 80° C. with stirring. To the resulting solution, 15 g of ion exchange water were added dropwise and the mixture was aged for 3 h. The obtained suspension was cooled, filtered, washed with water, dried at 110° C. for 1 day and calcined at 300° C. for 3 h in a flowing air. The calcined product was ground until it was able to pass through a sieve with a mesh width of 150 μm.

The ground product was analyzed for constituting elements thereof by fluorescent X-ray analysis and ICP emission analysis, a specific surface area thereof by the BET method and a particle size distribution thereof. Thus, a catalyst A having the composition, specific surface area, average particle diameter (median diameter) and particle size distribution shown in Table 1 was obtained.

PREPARATION EXAMPLE 2

Preparation of Catalyst B

A catalyst B having the composition, specific surface area, average particle diameter (median diameter) and particle size distribution shown in Table 1 was obtained by repeating the same procedure as in Preparation Example 1 except that 35 g of titanium tetraisopropoxide and 11.6 g of the isopropanol solution of zirconium tetrapropoxide were used.

PREPARATION EXAMPLE 3

Preparation of Catalyst C

A catalyst C having the composition, specific surface area, average particle diameter (median diameter) and particle size distribution shown in Table 1 was obtained by repeating the same procedure as in Preparation Example 1 except that 41.8 g of titanium tetraisopropoxide were used, and 2.1 g of niobium pentabutoxide were used in place of 2.3 g of the isopropanol solution of zirconium tetrapropoxide.

PREPARATION EXAMPLE 4

Preparation of Catalyst D

A catalyst D having the composition, specific surface area, average particle diameter (median diameter) and particle size distribution shown in Table 1 was obtained by repeating the same procedure as in Preparation Example 1 except that 1.9 g of germanium tetraisopropoxide were used in place of 2.3 g of the isopropanol solution of zirconium tetrapropoxide.

PREPARATION EXAMPLE 5

Preparation of Catalyst E

A separable flask was charged with 34 g of titanium oxysulfate and 270 g of an aqueous silica sol solution (3 g as silica). The mixture was heated to 90° C. with stirring. After confirming that titanium oxysulfate was dissolved, aqueous ammonia was added dropwise to the solution (90° C.) to neutralize the solution, which was then stirred for 2 h. The obtained precipitated product was filtered, washed with 1 L of ion exchange water four times, dried at 130° C. overnight. The dried product was ground until it was able to pass through a sieve with a mesh width of 150 μm. The ground product was analyzed for constituting elements thereof by fluorescent X-ray analysis and ICP emission analysis, a specific surface area thereof by the BET method and a particle size distribution thereof. Thus, a catalyst E having the composition, specific surface area, average particle diameter (median diameter) and particle size distribution shown in Table 1 was obtained.

PREPARATION EXAMPLE 6

Preparation of Catalyst F

A catalyst F having the composition, specific surface area, average particle diameter (median diameter) and particle size distribution shown in Table 1 was obtained by repeating the same procedure as in Preparation Example 1 except that 2.2 g of tetraethyl silicate were used in place of 2.3 g of the isopropanol solution of zirconium tetrapropoxide.

COMPARATIVE PREPARATION EXAMPLE 1

Preparation of Catalyst G

A separable flask was charged with 250 g of isopropanol, to which 46 g of titanium tetraisopropoxide were added. The mixture was heated to 80° C. with stirring. To the resulting solution, 15 g of ion exchange water were added dropwise, and the mixture was aged for 3 h. The obtained suspension was cooled, filtered, washed with water, dried at 110° C. for 1 day and calcined at 300° C. for 3 h in a flowing air. The calcined product was ground until it was able to pass through a sieve with a mesh width of 150 μm. The ground product was analyzed for constituting elements thereof by fluorescent X-ray analysis and ICP emission analysis, a specific surface area thereof by the BET method and a particle size distribution thereof. Thus, a catalyst G having the composition, specific surface area, average particle diameter (median diameter) and particle size distribution shown in Table 1 was obtained.

TABLE 1

| | Solid acid catalyst | | Composition (M*/Ti) (mass ratio) |
|---|---|---|---|
| Preparation Example 1 | Catalyst A | Ti—Zr | 0.065 |
| Preparation Example 2 | Catalyst B | Ti—Zr | 0.412 |
| Preparation Example 3 | Catalyst C | Ti—Nb | 0.061 |
| Preparation Example 4 | Catalyst D | Ti—Ge | 0.061 |
| Preparation Example 5 | Catalyst E | Ti—Si | 0.138 |
| Preparation Example 6 | Catalyst F | Ti—Si | 0.044 |
| Comparative Preparation Example 1 | Catalyst G | Ti | 0 |

| | Specific surface area (m$^2$/g) | Average particle diameter (μm) | Amount of particles of 1 μm or less (%) |
|---|---|---|---|
| Preparation Example 1 | 172 | 9.9 | 10.9 |
| Preparation Example 2 | 349 | 6.5 | 19.5 |
| Preparation Example 3 | 162 | 5.7 | 14.6 |
| Preparation Example 4 | 246 | 7.6 | 7.8 |
| Preparation Example 5 | 262 | 13.1 | 3.9 |
| Preparation Example 6 | 293 | 6.1 | 7.9 |
| Comparative Preparation Example 1 | 146 | 13.2 | 9.4 |

Note:
M* is an element (except titanium) belonging to Groups 4, 5 and 14 of the long form of the periodic table Example 1

In a rotary type autoclave, 400 g of stearic acid and 0.5% by mass, based on the raw material fatty acid, of the catalyst A obtained in Preparation Example 1 were charged, and the mixture was heated to 260° C. while flowing nitrogen therethrough. When the reaction temperature of 260° C. was reached, the flow of nitrogen was shifted to a flow of dimethylamine. Thus, dimethylamine was introduced into the reaction system at a flow rate of 35 to 38 L per hour (corresponding to 1.1 to 1.2 mol/h per 1 mol of the raw material fatty acid). The reaction was continued until the acid value of the reaction product reached 0.2 or less. The time required until the acid value of the reaction product reached 0.2 or less was 3.0 h. A filter paper ("No. 5C" available from Advantech® Group) was fitted on a filter plate of a cylindrical filtering device (2.8 cm in diameter×100 cm in height) and kept at a temperature of 70° C. The whole amount of the product finally obtained by the reaction was charged in the filtering device and was subjected to constant pressure filtration by applying a pressure of 0.3 MPaG (G: gauge pressure) for the removal of the catalyst. As a result, it took 13 min from the start of the application of the pressure to obtain 400 g of a filtrate (N,N-dimethylstearoylamide).

Comparative Example 1

The same procedure as in Example 1 was conducted except that the catalyst G prepared in Comparative Preparation Example 1 was used in place of the catalyst A. The time required until the acid value of the reaction product reached 0.2 or less was 3.4 h. The catalyst was separated in the same procedure as in Example 1. As a result, it took 40 min to obtain 400 g of the filtrate (N,N-dimethylstearoylamide).

Examples 2 to 5 and Comparative Examples 2 and 3

Reactions were carried out in the same manner as in Example 1 except that 400 g of lauric acid were used in place of 400 g of stearic acid, the catalysts B to E and G prepared in Preparation Examples 2 to 5 and Comparative Preparation Example 1, respectively, and commercially available titanium dioxide "MC-150" available from Ishihara Sangyo Kaisha, Ltd., (specific surface area: 283 m$^2$/g; average particle diameter: 1.0 μm; content of particles with particle diameter of 1 μm: 50.7%; catalyst H) were each used in place of the catalyst A, and dimethylamine was introduced into the reaction system at a flow rate of 49 to 54 L per hour (corresponding to 1.1 to 1.2 mol/h per 1 mol of the raw material fatty acid). The products finally obtained by the reaction were each subjected to separation of the catalyst from the reaction product in the same filtration procedure as in Example 1. The time required until the acid value of the reaction product reached 0.2 or less and the time required for obtaining 400 g of a filtrate (N,N-dimethyllauroylamide) are shown in Table 2.

TABLE 2

| | Catalyst Used | Reaction Time (h) | Filtration Time (min) |
|---|---|---|---|
| Example 2 | Catalyst B | 4.1 | 13 |
| Example 3 | Catalyst C | 4.0 | 11 |
| Example 4 | Catalyst D | 3.9 | 11 |
| Example 5 | Catalyst E | 3.9 | 12 |
| Comparative Example 2 | Catalyst G | 4.3 | 49 |
| Comparative Example 3 | Catalyst H | 4.0 | 9,120 |

Example 6

A reaction was carried out in the same manner as in Example 2 except that the catalyst F prepared in Preparation Example 6 was used in place of the catalyst B, and the catalyst was charged in an amount of 1.0% by mass (on the basis of the raw material fatty acid). The acid value of the reaction product was 0.06 when the reaction was carried out for 3 h. The product finally obtained by the reaction was subjected to separation of the catalyst in the same filtration procedure as in Example 2. As a result, it took 21 min to obtain 400 g of a filtrate (N,N-dimethyllauroylamide).

Comparative Example 4

A reaction was carried out in the same manner as in Example 6 except that the catalyst G prepared in Comparative Preparation Example 1 was used in place of the catalyst F. The acid value of the reaction product was 0.07 when the reaction was carried out for 3 h. The product finally obtained by the reaction was subjected to separation of the catalyst in the same filtration procedure as in Example 6. As a result, it took 146 min to obtain 400 g of a filtrate (N,N-dimethyllauroylamide).

Example 7

A reaction was carried out in the same manner as in Example 1 except that 400 g of lauric acid were used in place of 400 g of stearic acid, and dimethylamine was introduced into the reaction system at a flow rate of 94 to 98 L per hour (corresponding to 2.1 to 2.2 mol/h per 1 mol of the raw material fatty acid). The time required until the acid value of the reaction product reached 0.2 or less was 3.8 h. The catalyst was separated in the same filtration procedure as in Example 1. As a result, it took 10 min to obtain 400 g of a filtrate (N,N-dimethyllauroylamide).

Example 8

A reaction was carried out in the same manner as in Example 2 except that monomethylamine was used in place of dimethylamine. The time required until the acid value of the reaction product reached 0.2 or less was 4.0 h. The product finally obtained by the reaction was subjected to separation of the catalyst in the same filtration procedure as in Example 2. As a result, it took 25 min to obtain 400 g of a filtrate (N-methyllauroylamide).

The invention claimed is:

1. A process for producing an aliphatic carboxylic acid amide, comprising the step of reacting an aliphatic carboxylic acid or an alkyl ester thereof containing an alkyl group having 1 to 4 carbon atoms with a mono- or dialkylamine containing an alkyl group or groups having 1 to 4 carbon atoms in the presence of a solid acid catalyst comprising titanium oxide as a main component, and an oxide or oxides of at least one element selected from the group consisting of elements (except titanium) belonging to Groups 4, 5 and 14 of the long form of the periodic table, said catalyst having an average particle diameter of 2 μm or more;

wherein a content of the titanium oxide in the solid acid catalyst is not less than 30% by mass in terms of metallic titanium; and wherein a proportion of the at least one element selected from the group consisting of elements (except titanium) belonging to Groups 4, 5 and 14 of the long form of the periodic table relative to the titanium is from 0.005 to 0.412 in terms of mass ratio.

2. The process for producing an aliphatic carboxylic acid amide according to claim 1, wherein the at least one element selected from the group consisting of elements (except titanium) belonging to Groups 4, 5 and 14 of the long form of the periodic table is at least one element selected from the group consisting of zirconium, niobium, silicon and germanium.

3. The process for producing an aliphatic carboxylic acid amide according to claim 1, wherein the solid acid catalyst contains particles having a diameter of 1 μm or less in an amount of 30% by volume or less on the basis of the whole particles.

4. The process for producing an aliphatic carboxylic acid amide according to claim 1, wherein the aliphatic carboxylic acid is a linear or branched aliphatic carboxylic acid having 6 to 24 carbon atoms.

5. The process for producing an aliphatic carboxylic acid amide according to claim 1, wherein the content of the titanium oxide in the solid acid catalyst is from 30 to 59.5% by mass in terms of metallic titanium.

6. The process for producing an aliphatic carboxylic acid amide according to claim 1, wherein the process has a filtration time of 25 minutes or less when the aliphatic carboxylic acid amide is charged in a filtering device with a diameter of 2.8 cm, a height of 100 cm, and a No. 5C filter paper at a temperature of 70° C. and subjected to constant pressure filtration of 0.3 MPaG.

\* \* \* \* \*